Figure 1:
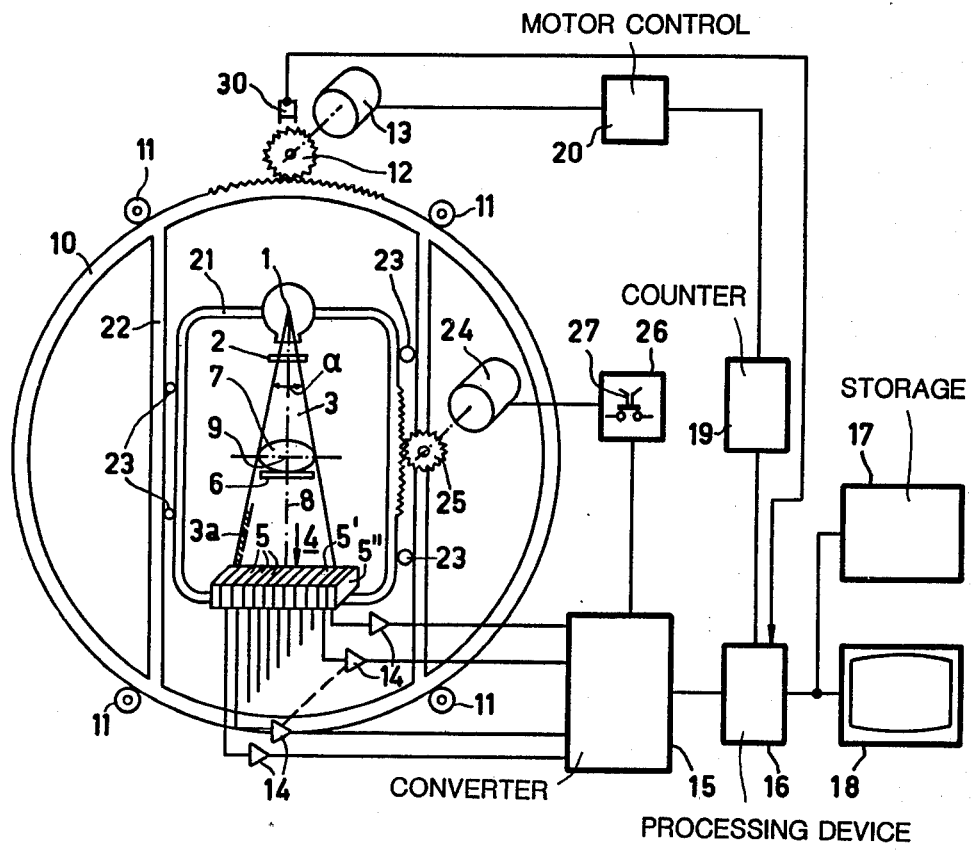

United States Patent [19]

Op de Beek

[11] Patent Number: 4,460,961
[45] Date of Patent: Jul. 17, 1984

[54] METHOD OF AND DEVICE FOR DETERMINING A RADIATION ABSORPTION DISTRIBUTION IN A PART OF A BODY

[75] Inventor: Johannes C. A. Op de Beek, Eindhoven, Netherlands

[73] Assignee: U.S. Philips Corporation, New York, N.Y.

[21] Appl. No.: 73,572

[22] Filed: Sep. 7, 1979

[30] Foreign Application Priority Data

Mar. 14, 1979 [NL] Netherlands .................. 7902015

[51] Int. Cl.³ .......................................... G06F 15/42
[52] U.S. Cl. .................................. 364/414; 378/901
[58] Field of Search ........................ 364/414; 382/6; 378/901, 21, 51

[56] References Cited

U.S. PATENT DOCUMENTS

| | | | |
|---|---|---|---|
| 4,052,619 | 10/1977 | Hounsfield | 364/414 |
| 4,066,903 | 1/1978 | Le May | 364/414 |
| 4,138,611 | 2/1979 | Hounsfield | 364/414 |
| 4,149,259 | 4/1979 | Kowalski | 364/414 |
| 4,274,140 | 6/1981 | Watson | 364/414 |

Primary Examiner—Errol A. Krass
Attorney, Agent, or Firm—Jack E. Haken

[57] ABSTRACT

The invention relates to a method of and a device for determining a radiation absorption distribution in a part of a body. Per measuring value a contribution of the absorption value in each element of a matrix imagined in the part is calculated. It is demonstrated that this contribution equals the value of the measuring value multiplied by a weighting factor. The weighting factor is a function of the distance between the element and the measuring path along which the measuring value is determined. A calculation method of this kind enables fast on-line calculation of an absorption distribution and the complete reconstruction of the absorption distribution is laid down in a hardware circuit. Complex operations such as F.F.T., convolution and interpolation are not required.

7 Claims, 6 Drawing Figures

METHOD OF AND DEVICE FOR DETERMINING A RADIATION ABSORPTION DISTRIBUTION IN A PART OF A BODY

The invention relates to a method of determining a radiation absorption distribution in a part of a body, the part of the body being irradiated in a plurality of directions by at least one narrow beam of radiation which penetrates the body, the radiation having passed through the body being measured for each direction, measuring values being derived therefrom which are a measure for the radiation attenuation of the beam along a measuring path followed by the beam, said measuring values being used to derive absorption values which are associated with elements of a matrix in which the radiation absorption distribution is displayed.

The invention furthermore relates to a computer tomography device for performing the method, said device comprising at least one source for generating the radiation penetrating the body, a detector device for detecting the radiation and for supplying measuring values, at least one supporting frame for the source and the detector device, drive means for moving at least the source in order to scan the part of the body by means of the radiation beam, a processing device for determining absorption values from the measuring values, a storage device for the storage of the absorption values, and a display device for the display of the absorption values.

A method and a computer tomography device of the described kind are known from U.S. Pat. No. 3,983,398. The described method and notably the processing of the measuring values therein is complex. This is because the processing of the measuring data comprises the following steps:

- the sorting/ordering of measuring values so that they are ultimately in a sequence as if they had been measured along parallel measuring paths,
- the interpolation between the measuring values thus ordered in order to determine fictitious measuring values which would have been measured along equidistant measuring paths,
- the convolution of the fictitious measuring values with a series of numbers, so that a series of convoluted values is produced,
- calculating a contribution of each convoluted value to an element which is fully or partly situated on a path associated with the fictitious measuring value, said calculation involving an interpolation between "adjacent" convoluted values.

It will be clear that a processing device for performing the steps described above is also complex.

The invention has for its object to provide a method and a computer tomography device in which the absorption values are determined from the measuring values in a simple (and quick) manner so that a radiation absorption distribution becomes available substantially immediately after determination of a last measuring value and can be displayed on the display device.

The invention also has for its object to provide a method and a computer tomography device in which the accuracy of the absorption values to be determined is not adversely affected by interpolations and the like.

To this end, the method in accordance with the invention is characterized in that for each measuring value a contribution in the absorption value of each element is separately calculated, the measuring value being multiplied by a weighting factor which is a function of the shortest distance between the element for which the contribution is calculated and the measuring path along which the measuring value is determined, after which the absorption value in an element is determined by the summing per element of the contributions thus obtained.

The method in accordance with the invention is based on the recognition of the basis underlying reconstruction algorithms used in the field of computer tomography. It can be deduced that an absorption distribution $f(r,\phi)$, in which $r$ and $\phi$ are the coordinates in a plane with a polar coordinate system, can be expressed in the following formule:

$$f(r, \phi) = \int_0^{2\pi} \int_{-\infty}^{\infty} g(r', \theta) \cdot q(r \cdot \cos(\phi - \theta) - r') dr' d\theta \quad (1)$$

in which $$q(r) = \int_{-\infty}^{\infty} |R| \cdot \exp(-2\pi i r R) dR \quad (2)$$

and $g(r',\theta)$ are measuring values along paths which pass the origin of the coordinate system $(r,\phi)$ at a distance $r'$ and at an angle $\theta$, $\theta$ ranging from 0 to $2\pi$. The invention is based on the recognition of the fact that a measuring value $g(r_1, \theta_1)$ in a point $(r,\phi)$ makes a contribution equal to $$\Delta f(r,\phi;r_1,\theta_1) = g(r_1,\theta_1) \cdot q(r \cdot \cos(\phi - \theta_1) - r_1). \quad (3)$$

The contribution $\Delta f$ according to (3), therefore, equals the measuring value $g(r_1, \theta_1)$ which is mutliplied by a function of the shortest distance d between the point $(r,\phi)$ and the measuring path along which the measuring value $g(r_1, \theta_1)$ is determined. Thus, it will be clear that the absorption value in an element is determined by determination, per measuring value separately, of said contribution $\Delta f$ per element, after which all contributions $\Delta f$ per element are summed.

The weighting factors $q(r \cdot \cos(\phi - \theta_1) - r_1)$ or $(q(d))$ are determined from (2) where the integral is calculated between the values $+R_n$ and $-R_n$, $R_n$ being equal to $\frac{1}{2}a$, a being the largest distance between the centers of two adjacent measuring paths in the body. It then follows from (2) that:

$$q(d) = \frac{\sin(\pi \cdot d/a)}{2 \cdot \pi \cdot a.d.} + \frac{\cos(\pi \cdot d/a) - 1}{2(\pi \cdot d)^2} \quad (4)$$

Therefrom, for each d exactly which weighting factor is associated with the element in $(r, \phi)$ and with the measuring value $g(r_1, \theta_1)$ can be determined. Thus, for each measuring value the exact contribution $\Delta f$ of an absorption value $f(r,\phi)$ can be calculated, approximations by interpolations and the like being superfluous. Furthermore, the complex steps such as the sorting of measuring values, convolution of measuring values and interpolations are avoided.

A method in accordance with the invention, where a plane of a body is irradiated in a plurality of directions by means of a flat, fan-shaped radiation beam which can be divided into a number of narrow radiation beams so that the radiation having passed through the body is simultaneously measured along the measuring paths associated with the radiation beams, is characterized in that from the simultaneously obtained measuring values a contribution in the absorption value of an element of a two-dimensional matrix is separately and simultaneously calculated.

A method of this kind offers the advantage that, thanks to the simultaneous (parallel) calculation of contributions in absorption values, a fast reconstruction of an absorption distribution in a plane of a body is possible without complex arithmetic operations (such as interpolations, convolutions and Fourier transforms) being required.

A computer tomography device for performing a method in accordance with the invention is characterized in that the processing device comprises

- a weighting factor generator for generating weighting factors as a function of the coordinates of an element for which a contribution is calculated and of the coordinates of the measuring path, along which a measuring value is determined, which are applied to the weighting factor generator,
- at least one multiplier circuit for multiplying the measuring value and the associated weighting factor, for which purpose the multiplier circuit is connected to the weighting factor generator, and
- a summing device, an input of which is connected to an output of the multiplier circuit in order to sum the contributions calculated per element, an output of said summing device being connected to the storage device.

A computer tomography device of this kind offers the advantage that an image of a part of the irradiated body can be realized by means of simple means.

An embodiment of a computer tomography device in accordance with the invention in which the detector device comprises an array of detectors which are adjacently arranged within the X-ray beam and which offers the advantage that a quick reconstruction of the radiation absorption distribution in a plane of a body is possible due to the parallel processing of measuring values is characterized in that the weighting factor generator is divided into a number of mutually independent subgenerators which at least equals the number of detectors which simultaneously supply a measuring value, at least one multiplier circuit being provided per subgenerator.

A further embodiment of a computer tomography device for performing the method in accordance with the invention is characterized in that each subgenerator comprises a weighting factor memory and a circuit for forming, from the coordinates of a measuring path and an element to be applied thereto, an address for searching a weighting factor in the weighting factor memory. It has been found that an embodiment of this kind is advantageous because the weighting factors are determined on the basis of the actual coordinates of the measuring path associated with the measuring value to be processed, so that only an as small as possible deviation between measuring arrangement and calculation values used for the reconstruction is accepted.

A preferred embodiment of a computer tomography device in accordance with the invention is characterized in that per circuit there are provided a number of multiplier circuits and a same number of adding circuits which equal the number of elements in a row of the matrix and which are assigned to an element number in the row, the outputs of the adding circuits being connected, via a multiplex circuit, to the weighting factor memory, the output of which is connected, via a demultiplex circuit, to the successive multiplier circuits associated with the adding circuit, an outputs of all multiplier circuits assigned to one and the same element number being connected to an input of a summing circuit, the number of summing circuits in the summing device being equal to the number of elements in the row of the matrix, an output of said summing circuit being connected, via an output adding circuit, to a one-dimensional storage space of the storage device for the storage of absorption values of elements of a column of the matrix. An embodiment of this kind is attractive in that per detector a contribution is calculated each time simultaneously for each element of a row of the matrix, said contribution being applied in summed form only via the summing circuits to the individual elements in said row, so that a very fast reconstruction of the absorption distribution is possible while at the same time the storage space required is limited.

The invention will be described in detail hereinafter, by way of example, on the basis of an embodiment of a computer tomography device which is diagrammatically shown in a drawing.

Figure 2:
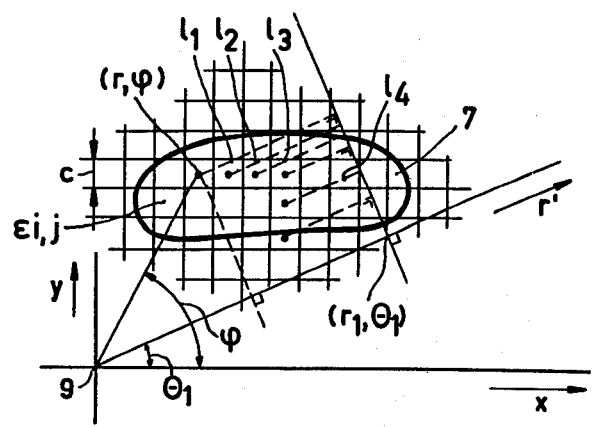
Figure 3:
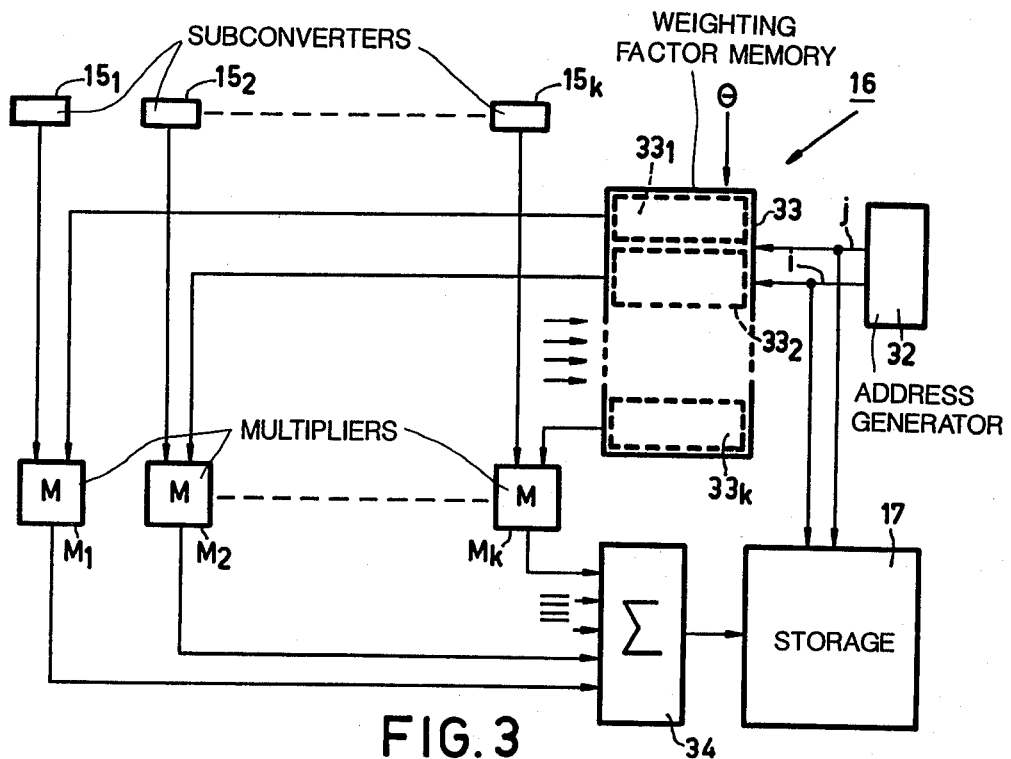
Figure 4:
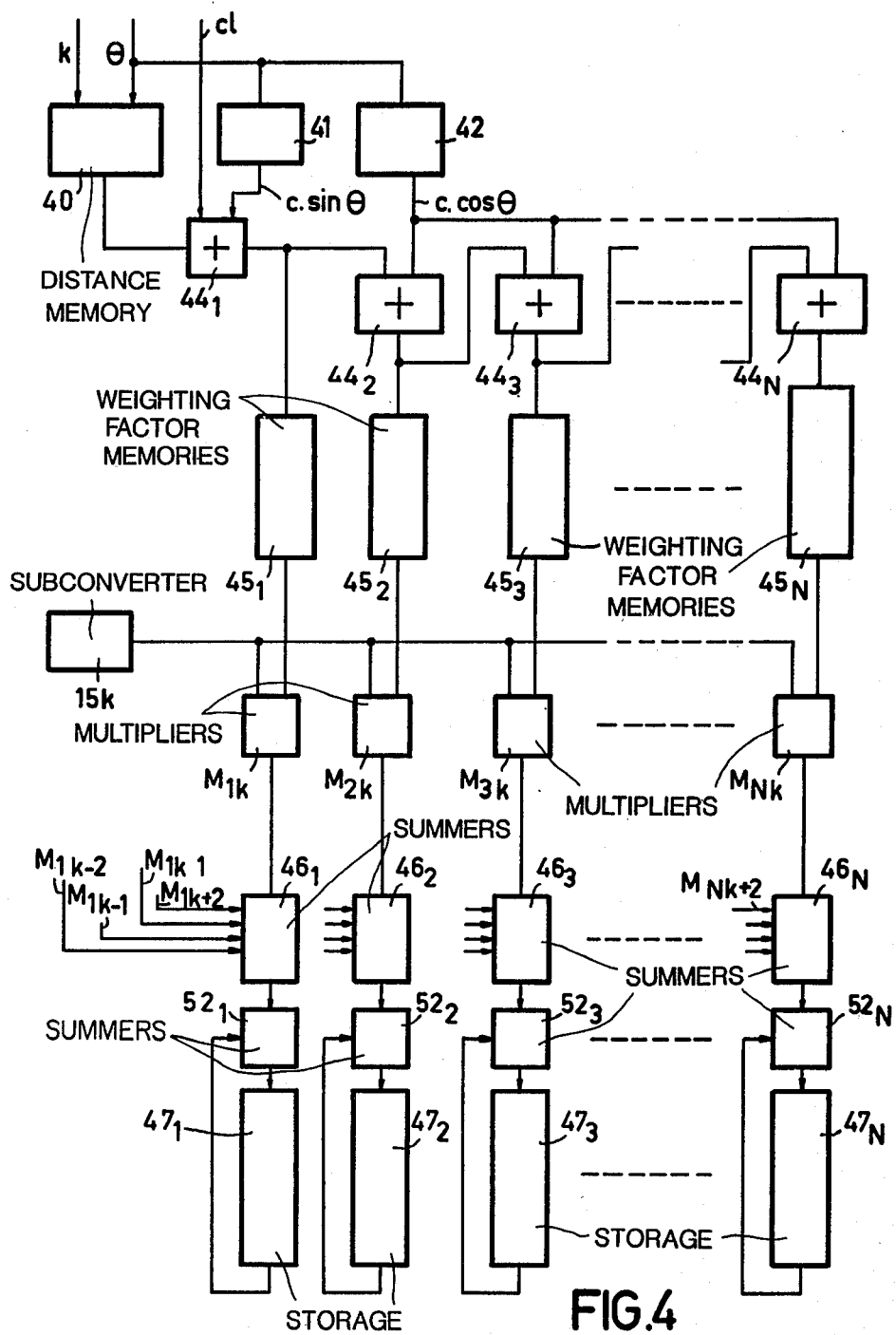
Figure 5:
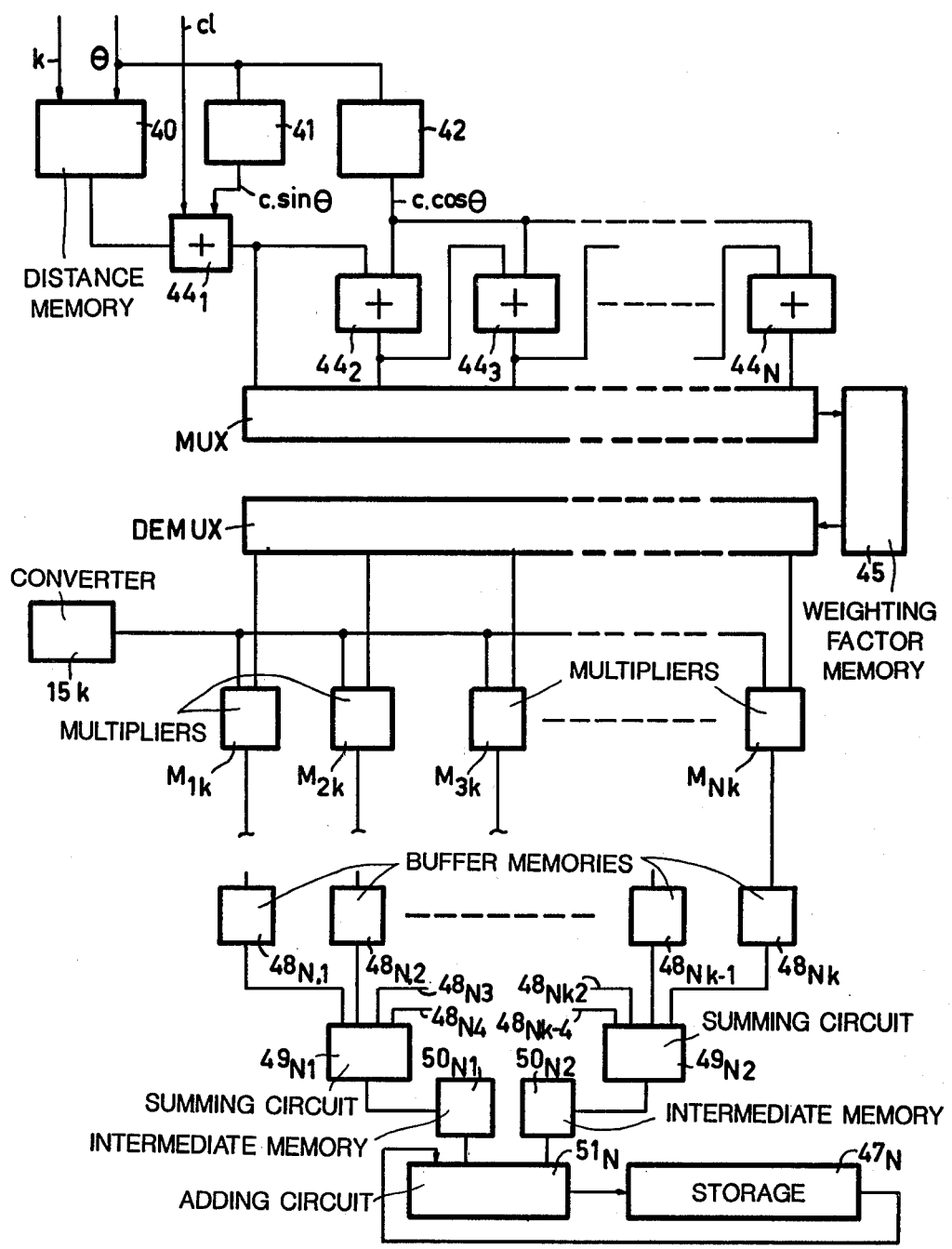
Figure 6:
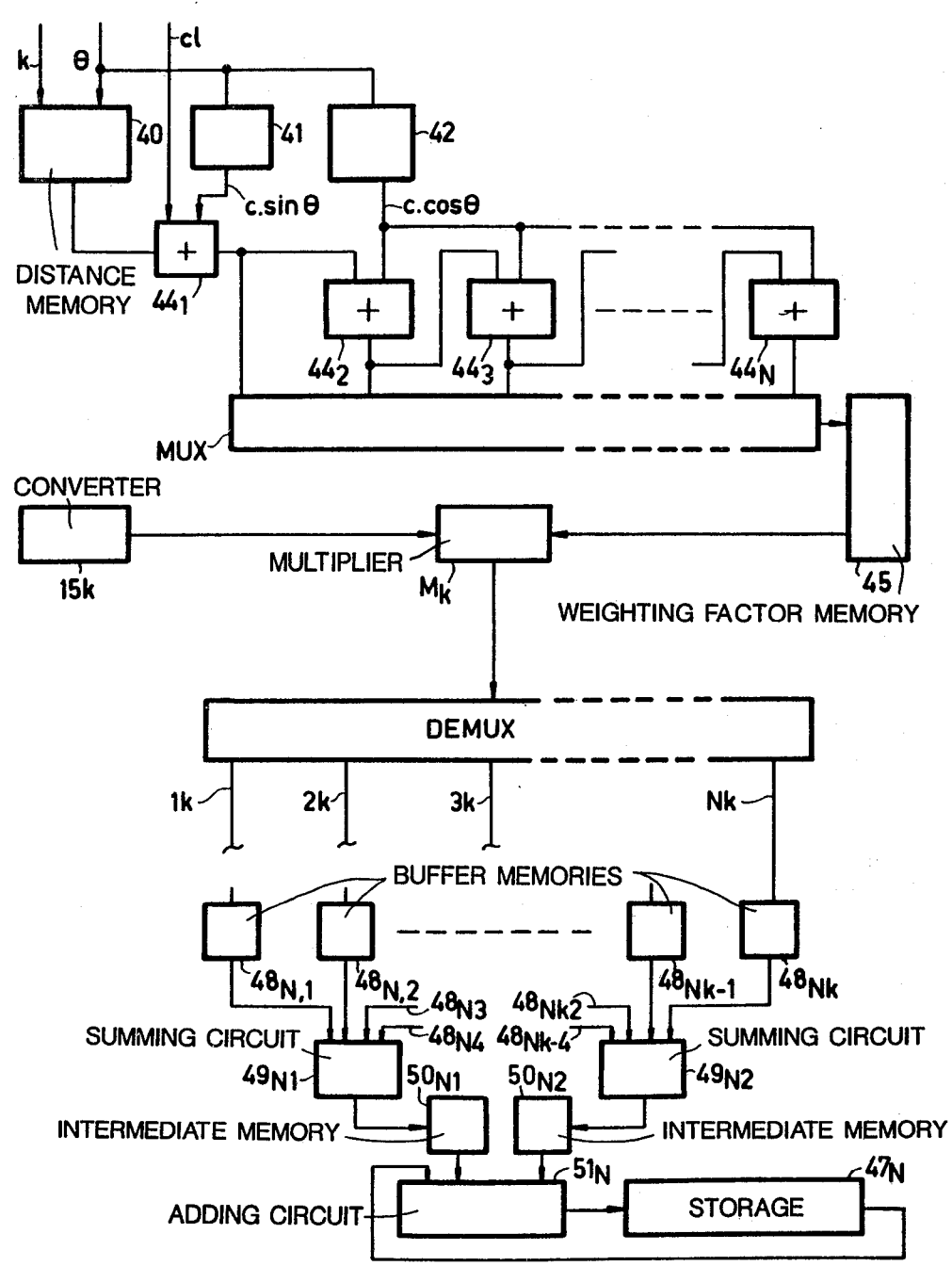

FIG. 1 diagrammatically shows a computer tomography device in accordance with the invention, FIG. 2 shows a matrix of elements on the basis of which the determination of contributions of absorption values in accordance with the invention will be described, FIG. 3 shows a block diagram of an embodiment of a processing device and a storage device for the computer tomography device of FIG. 1, FIG. 4 shows a comparatively detailed block diagram of a preferred embodiment of a part of the processing device and a storage device in accordance with the invention, FIG. 5 shows a modified block diagram of a part of the processing device and a part of the storage device of FIG. 4, FIG. 6 shows a further modified block diagram of the part shown in FIG. 5.

A computer tomography device as diagrammatically shown in FIG. 1 comprises a radiation source 1 which is preferably an X-ray source, but which may alternatively be a radioactive isotope, for example, Am 241. Using an aperture 2, the radiation emitted by the radiation source 1 is collimated to form a diverging radiation beam 3 which is situated in one plane, the thickness of the radiation beam 3 in the direction perpendicular to the plane being, for example, between 3 and 25 mm and the divergence thereof in the plane being determined by the angle $\alpha$. The radiation beam 3 is incident on a detector array 4 which consists of separate detectors 5 which measure the radiation and which define radiation beams 3a, the width of and the distance between the individual detectors defining the spatial accuracy with which an object 7 on an object table 6 is scanned. The detector array 4, being symmetrically positioned with respect to a central ray 8, comprises, for example, 300 detectors 5, the distance between the centres of two detectors 5 amounting to a few millimeters. The detector can alternatively be made of a long, gas-filled ionization chamber in which electrodes which detect separate zones are arranged in a row. The object 7 is slidable perpendicularly to the plane of the radiation beam 3 in the longitudinal direction of the axis 9, which is situated inside the object 7, and the central axis of the circular supporting frame 10, so that different layers of the object 7 can be irradiated.

The system formed by the radiation source 1 and the detector array 4 is arranged to be rotatable around the axis 9, so that a layer of the object 7 can be irradiated by means of the radiation beam 3 in different directions which are situated in the layer. The rotation of the supporting frame 10, being guided by means of the bearing 11, is realized by means of drive means such as a gearwheel 12 and a motor 13. The rotation of the supporting frame 10 can take place continuously as well as intermittently; in the latter case, the radiation source 1 is flashed by after each step.

The measuring signals of the detectors 5 are amplified by means of an amplifier 14 and are applied to a signal converter 15 in which the measuring signals are corrected in known manner for "offset", are related to a reference value, are digitized, are subjected to logarithmation and are calibrated on the basis of logarithmation and calibration tables incorporated in the signal converter. Digital measuring values are applied from the output of the converter 15 to the processing circuit 16. The converter preferably comprises a subconverter 15 per detector, all subconverters operating in parallel. The digitized measuring values are converted, by means of the processing device 16, into absorption values which represent a reconstruction image and which are stored in a storage device 17. The calculated absorption values can be displayed on a display device, for example, a monitor 18. A counter 19 counts the number of measuring values applied to the arithmetic unit 16 per measuring series. As soon as the number of measuring values corresponds to the number of detectors 5, a control circuit 20 is activated which briefly drives the motor 13, thus causing rotation of the supporting frame 10. Subsequently, the next measuring series is performed etc. Using an optical transducer 30, the angular shift $\theta$ between the successive measuring series is determined by the counting of the teeth of the gearwheel 12. The pulses generated by the transducer 30 are applied to the processing device 16, so that the coordinates of all measuring paths can be determined in combination with the data concerning the geometrical construction of the supporting frame 10 and the source 1 with the detector device 4 which are laid down in the processing device.

It has been found that the distance between the radiation source 1 and the object 7 is preferably adaptable to the diameter of the object 7. To this end, the system formed by the radiation source 1 and the detector array 4 is mounted on a support 21 which can be displaced along the guide rails 22 on bearings 23 by means of a gearwheel drive 25 which is coupled to a motor 24. A control circuit 26 can be operated, for example, by means of a manual switch 27; however, the circuit 26 can also be automatically operated. Prior to the start of the measurement, the measuring signals of two detectors 5' and 5'' are applied to the control circuit 26 via the signal converter 15. The support 21 is displaced so that the measuring signal of the detector 5'' is maximum, whilst the measuring signal of the detector 5' has a slightly lower value. In that case the detector 5'' receives radiation which does not pass through the object 7 but rather fully through the space surrounding the object 7, while the radiation measured by the detector 5' has been attenuated by the object 7. The control circuit 26 is subsequently locked in order to maintain the distance between the radiation source 1 and the axis of rotation 9 constant during the exposure.

The determination of a contribution in an element having the coordinates $(r,\phi)$ of a measuring value determined along the measuring path having the coordinates $(r_1, \theta_1)$ will be described with reference to FIG. 2 which shows a matrix of elements $\epsilon$ which is imagined on the object 7 (FIG. 1).

From a publication in the Proceedings of the National Academy of Science, U.S.A., Vol. 68, No. 9, pages 2236-2240, September 1971, it is known that an absorption distribution $f(r,\phi)$ in a plane having the polar coordinates $(r,\phi)$ can be expressed in the formule:

$$f(r, \phi) = \int_0^{2\pi} \int_{-\infty}^{\infty} g(r', \theta) \cdot q(r \cdot \cos(\phi - \theta) - r') dr' d\theta \quad (1)$$

in which $$q(r) = \int_{-\infty}^{\infty} |R| \cdot \exp(-2\pi i r R) \quad (2)$$

and $g(r', \theta)$ are measuring values of radiation absorption along measuring paths which pass the origin 9 of the system of coordinates $(r,\phi)$ at a distance $r'$ at an angle $\theta$, $\theta$ ranging up to $2\pi$ and $r'$ being from 0 to $r_{max}$. (The origin 9 is assumed to be situated outside the object 7 for the sake of clarity of FIG. 2).

Using the formulas (1) and (2), the elementary contribution of a measuring value $g(r_1, \theta)$ to be absorption value in the element $\epsilon$ having the coordinates $(r,\phi)$ can be calculated. Assume that:

$g(r_1, \theta_1) \neq 0$ for $(r_1, \theta_1)$ and $g(r, \theta) = 0$ for all other $r$ and $\theta$.

The contribution made by the measuring value $g(r_1, \theta_1)$ follows from formule (1) by omission of the integrals:

$$\Delta f(r,\phi; r_1,\theta_1) = g(r_1,\theta_1) \cdot q(r \cos(\phi - \theta_1) - r_1) \quad (3)$$

The value $r_1 - r \cdot \cos(\phi - \theta_1)$ is the distance between the point $(r,\phi)$ and the measuring path which extends through the point $(r_1, \theta_1)$ and along which the measuring value $g(r_1, \theta_1)$ is determined. The function $q(r)$ is a symmetrical function (see formule 2), which means that $q(d) = q(-d)$. The weighting factors $q(d)$ are determined via formule (2), the integral between the limits $-R_n$ and $+R_n$ being calculated, $R_n$ being determined by the width of the measuring path along which the measuring value is determined. If a is the largest distance between the centres of two substantially parallel measuring paths, $R_n$ must be chosen to equal $\frac{1}{2}a$. It then follows from (2) that:

$$q(d) = \frac{\sin(\pi \cdot d/a)}{2 \cdot \pi \cdot a \cdot d} + \frac{\cos(\pi \cdot d/a) - 1}{2(\pi \cdot d)^2} \quad (4)$$

The absorption value in a point $(r,\phi)$ can thus be calculated from:

$$f(r, \phi) = \sum_{r'=0}^{r_{max}} \sum_{\theta=0}^{2\pi} \Delta f(r, \phi; r', \theta) \quad (5)$$

The absorption value $f(r,\phi)$ is the sum of all contributions, $\Delta f$, each contribution being equal to the product of the measuring value g(r', θ) with the weighting factor q(d), d being the distance between the coordinates (r,φ) and the measuring path through (r', θ).

The representation of the elements ε in FIG. 2 is much too coarse with respect to the body 7. Actually, the dimension c of the (square) element is from 0.3 to 2 mm and the cross-section of the body is from 30 to 50 cm. Therefrom it follows that per measuring value a contribution is calculated for each element with a very accurate weighting factor (d can be very accurately determined).

FIG. 3 shows a block diagram of processing device 16 and a storage device 17. The processing device 16 comprises a weighting factor generator 31 which comprises an address generator 32 and a weighting factor memory 33. The address generator 32 comprises, for example, a pulse generator and two series-connected counters, the positions of which represent (x,y) coordinates of the elements $\epsilon_{ij}$ (FIG. 2) of the matrix imagined on the object 7 for which a contribution in the absorption values must be calculated. The measuring value $g(r_1,\theta), g(r_2,\theta), \ldots g(r_k,\theta)$ of each subconverter $15_1, 15_2, \ldots 15_k$ is applied to multiplier circuits $M_1, M_2, \ldots M_k$, which also receive the weighting factor q associated with the element $\epsilon_{ij}$ and the angle θ (derived via the location detector 30, FIG. 1). The weighting factor memory 33 is effectively subdivided (for fast operation) into k different weighting factor memories $33_1, 33_2, \ldots 33_k$ which operate in parallel and each of which is associated with a relevant detector $5_1, 5_2, \ldots 5_k$. The outputs of the multipliers $M_1, M_2, \ldots M_k$ on which the contributions Δf(i,j;k,θ) appear simultaneously (i, j: coordinates of the relevant element, k: detector number, and θ: angular position of a (reference) detector) are connected to a summing device 34 which sums all contributions and adds the sum to the absorption value which may already be present in the element $\epsilon_{i,j}$ after a preceding calculation.

After the address generator 32 has passed through all addresses (i, j), a next measurement is performed for a next angle θ.

The part of a preferred embodiment of a processing device in accordance with the invention which is shown in FIG. 4 serves to achieve fast processing of the measuring value obtained by means of a detector $5_k$ via the subconverter $15_k$. When the number of detectors is K, the part shown in FIG. 4 (and also the parts of the summing device 46, 52 and the storage device 47 yet to be described) should be present K times. The part of the processing device shown comprises a distance memory 40 in which a distance can be searched in a memory table on the basis of the data applied, for example, the detector number k and the angle θ. The distance to be searched is the distance from a fixed element ε of the matrix, for example, the element $\epsilon_{1,1}$. The successive distances between the elements of the row or a column in the matrix are determined as shown in FIG. 2 by repeated summing of the values c. cos θ and c. sin θ to the distance found via the distance memory 40. The distance $l_2$ equals: $l_1 - c. \cos\theta$; the distance $l_4$ equals: $l_1 - 3.c. \cos\theta + c. \sin\theta$; (FIG. 2).

Via the adder $44_1$, the distance is applied to a weighting factor memory $45_1$ and to a second adder $44_2$. The output of the adder $44_2$ is connected to a second weighting factor memory $45_2$ and to a third adder $44_3$. The above configuration is repeated N times, so that the distances of all elements $\epsilon_{1,j}$ of the first row of the matrix are present on the outputs of the adders $44_1, 44_2, \ldots$ $44_N$. (So, the number of elements ε per row is N). The distances are separately applied to the weighting factor memories $45_1, 45_2, \ldots 45_N$. On the outputs of the weighting factor memories $45_1, \ldots 45_N$ the weighting factors appear which have been searched on the basis of the distances (which actually constitute an address for the memories), each of said weighting factors being applied to the multipliers $M_{1k}, M_{2k}, M_{3k} \ldots M_{Nk}$. Furthermore, the multipliers $M_{1k}, \ldots M_{Nk}$ receive the measuring value originating from detector number k via the subconverter $15_k$. The products of the measuring value and the associated weighting factors obtained by the multipliers $M_{1k}, \ldots M_{Nk}$ are applied to the summing circuits $46_1, 46_2, \ldots 46_N$. The summing circuits $46_1, 46_2, \ldots 46_N$ also receive the products of the multiplier circuits of the identical parallel operating parts of the processing device (not shown). (Thus, for each detector k the contribution Δf is simultaneously calculated for each element in the same row of the matrix). All associated products thus applied to the summing circuit $46_1, \ldots 46_N$ are summed and applied to an output adding circuit $52_1, 52_2, 52_3, \ldots 52_N$, the output of which is connected to an associated one-dimensional shift register memory $47_1, 47_2, 47_3, \ldots 47_N$. The content of the "last" storage element of each memory $47_1, \ldots 47_N$ is also applied to the output adding circuit $52_1, \ldots 52_N$, so that the contributions of the measuring values of each detector calculated for an element can be added to a previously calculated absorption. The sum thus formed is stored in the first storage element after all absorption values in the memory have been shifted one location further. In each shift register memory $47_1$ the absorption values of the elements in a column of the matrix are stored. After termination of the preceding operation, the value c. sin θ is added to all distances in reaction to the supply of a clock pulse c1 to adder $44_1$, so that the distances of the elements $\epsilon_{2,j}$ of a next row of the matrix appear on the outputs of the adders $44_1, \ldots 44_N$, after which the contributions for the elements of the new row in the matrix are calculated in the described manner by means of these distances. Obviously, some operations can be performed in parallel; for example, during calculation of the contributions by the multiplier circuits $M_{1k}, \ldots M_{Nk}$ the distances for the next series of parallel calculations can already be determined.

FIG. 5 shows a modification of the processing section of FIG. 4. In the embodiment of the processing section, a weighting factor memory is connected to each adder $44_1, \ldots 44_N$. In order to limit the storage space required, the outputs can be connected to a multiplex circuit MUX, the output of which is connected to a weighting factor memory 45. The output of the weighting factor memory 45 is connected, via a demultiplex device DEMUX, to the inputs of the multipliers $M_{1k}, M_{2k}, \ldots M_{Nk}$. The saving of N-1 memories is accompanied by the fact that a slightly slower processing due to the time multiplex operation of the weighting factor memory 45 must be accepted. The part of the processing device shown in FIG. 5 deviates from that shown in FIG. 4 by a different lay-out of the summing device. In accordance with the modification shown in FIG. 5, each output of the multiplier circuits $M_{nk}$, where $1 \leq n \leq N$ and $1 \leq k \leq K$, is connected to an independent buffer memory $48_{nk}$, (the Figure shows only a few buffer memories for the element N). The buffer memories $48_{Nk}$ are divided into groups and per group a first summing circuit $49_{N1}, 49_{N2}$ is provided. The group-wise summed products are stored in intermediate memories $50_N$, $50_{N2}$, an intermediate memory $50N_1, \ldots 50_{N2}$ being provided for summing circuit $49_{N1}, \ldots 49_{N2}$. The outputs of the intermediate memories $50_{N1}, \ldots 50_{N2}$ are connected to a second adding circuit $51_N$ which sums the values originating from the intermediate memories 50. Furthermore, the output of the shift register memory $47_N$ is connected to the adding circuit $51_N$ for the reasons described with reference to FIG. 4. The use of the buffer memories 48 is necessary because otherwise synchronisation would be required between the multiplex device MUX and the demultiplex device DEMUX on the one hand and the operation of the summing circuit 49 on the other hand. Furthermore, the number of the inputs per summing circuit 49 is limited so that less severe requirements can be imposed as regards the calculation speed of the summing circuits 49.

Obviously, a compromise can be chosen between the part of the processing device shown in FIG. 4 and the modification thereof shown in FIG. 5. For example, two or more parallel operating multiplex and demultiplex devices can be used, the outputs and inputs of which lead to the adders 44 and multipliers M, respectively, which are divided into groups.

In FIG. 6 an embodiment of a part of the processing section has been shown, which is slightly modified relative to FIG. 5. As shown in FIG. 6 an output of the weighting factor memory 45 is connected to a multiplier $M_k$, to which also an output of subconverter $15_k$ is connected, which provides a measuring value. So the successive weighting factors generated by memory 45 are provided to multiplier $M_k$ and the products thus achieved are supplied to the demultiplex device DEMUX. Via the demultiplex device DEMUX the products are distributed via outputs 1k, 2k, ... Nk to the buffer memory $48_{nk}$ and from there processed as described above (FIG. 5). Of course the multiplex device MUX and the demultiplex device DEMUX should be synchronised properly. A time delay should exist between control signals applied to the multiplex- and demultiplex device respectively, which time delay is determined by the look-up speed of the memory 45 (FIG. 5) and by the multiplying speed of multiplier $M_k$ (FIG. 6). The shown embodiment in FIG. 6 has the advantage that relative to the embodiment shown in FIG. 5 a lot of multipliers M can be dispensed with. A number of N-1 multipliers will be saved, but on the other hand a slow down of data processing must be accepted as the multiplier $M_k$ will be a bottleneck in the dataflow, if such a multiplier is not N times faster than the multipliers $M_{ik}$ in FIG. 5.

The device and block diagrams described by way of example in the foregoing have a set-up so that a two-dimensional radiation absorption distribution is determined. However, the scope of the invention is greater and also enables the radiation absorption distribution to be determined in a three-dimensional space with comparatively simple means; the contribution of absorption in an element then always being equal to the measuring value multiplied by a weighting factor which is a function of the distance between the relevant element and the measuring path along which the measuring value is determined. Obviously, in order to obtain a homogeneous data density in the absorption distribution, a homogeneous distribution of measuring paths in the object part to be examined is required.

What is claimed is:

1. A method for determining a radiation absorption distribution in a part of the body of the type which comprises the steps of:
    irradiating the part of the body from a plurality of different directions with at least one narrow beam of radiation which penetrates the body;
    for each of the directions, measuring the attenuation of the beam along a measuring path which coresponds to the path of the beam through the body; and
    calculating radiation absorption values in elemental regions of a matrix of elemental regions of the body using the measured values of radiation attenuation;
    wherein, as an improvement, the radiation absorption value for each elemental region is calculated by separately determining the contribution of each measured attenuation value to the absorption value in each elemental region by separately multiplying each measured attenuation value by a weighting factor which is a function only of the shortest distance between the relevant elemental region and the measuring path along which the attenuation value was calculated; and
    for each elemental region summing the individual contributions to determine a total absorption factor for the elemental region.

2. A method as claimed in claim 1 wherein the step of irradiating the body comprises irradiating a plane of the body from a plurality of directions with a flat, fan-shaped radiation beam which is divided into a number of narrow radiation beams;
    simultaneously measuring the radiation attenuation values in the body for each of a plurality of said narrow radiation beams; and
    simultaneously calculating the contribution of the absorption value for each attenuation measurement for the elemental regions of a two-dimensional matrix.

3. The method of claim 2 wherein the matrix is divided into rows and columns and wherein the contribution to the absorption value for each elemental region in a row of the matrix is separately and simultaneously calculated.

4. A method as claimed in claim 2 wherein the contribution to the absorption value for every elemental region in the matrix is separately and simultaneously calculated.

5. Apparatus for computed tomography which calculates the distribution of absorption values in a region of a body comprising:
    source means for generating at least one narrow beam of penetrating radiation and for directing said radiation through the region of the body;
    detector means comprising at least one detector element for measuring the attenuation of each of such beams in the body and for supplying a signal representative thereof;
    means which cause the source to radiate the body from a plurality of different directions;
    location detector means for supplying a signal which represents the coordinates of a measuring path which each of said radiation beams follows through the body;
    signal processing means for calculating radiation absorption values in each elemental region of a matrix of elemental regions of the body from the measured values of attenuation and the coordinates of the measuring paths; and display means for displaying the distribution of absorption values in the body;

wherein, as an improvement, the signal processing means comprise:

weighting factor generator means for generating a set of weighting factors for each elemental region of the body and an associated set of measuring paths using the coordinates of the measuring paths wherein, the value of each of said weighting factors is a function only of the shortest distance between the associated elemental region and the relevant measuring path;

at least one multiplier for multiplying the attenuation value measured along each measuring path by an associated weighting factor; and summing means connected to receive outputs of the multiplier and to sum, for each elemental region, signals therefrom which represent weighted contributions of the measured attenuation values to the absorption value of that element.

6. A device as claimed in claim 5;

wherein the detector means comprise an array of detector elements which are adjacently arranged to measure attenuation along adjacent measuring paths;

the weighting factor generator means is divided into a number of mutually independent subgenerating means which simultaneously supply weighting values;

at least one multiplier circuit is present for each subgenerator; and the number of subgenerators is greater than or equal to the number of detector elements in the array.

7. A device as claimed in claim 6 wherein each subgenerator comprises a weighting factor memory and address forming means which determine the address of a weighting factor in the weighting factor memory from the coordinates of a measuring path and the identity of an associated elemental region of the body.

* * * * *